United States Patent [19]
Blazek et al.

[11] Patent Number: 5,447,161
[45] Date of Patent: Sep. 5, 1995

[54] MEASUREMENT DEVICE FOR NON-INVASIVE DETERMINATION OF BLOOD PRESSURE IN THE VEINS AND ARTERIES

[76] Inventors: Vladimir Blazek, Königshügel 31, 52074 Aachen; Hans-J. Schmitt, Hangstr. 34, 52076 Aachen, both of Germany

[21] Appl. No.: 103,801

[22] Filed: Aug. 10, 1993

[30] Foreign Application Priority Data

Aug. 14, 1992 [DE] Germany .......... 42 26 972.5

[51] Int. Cl.⁶ .......................................... A61B 5/022
[52] U.S. Cl. .......................................... 128/677
[58] Field of Search .......... 128/666–667, 128/672, 691, 694, 693

[56] References Cited

U.S. PATENT DOCUMENTS

| | | | |
|---|---|---|---|
| 3,920,004 | 11/1975 | Nakayama | 128/691 X |
| 4,144,878 | 3/1979 | Wheeler | 128/693 |
| 4,169,463 | 10/1979 | Piquard | 128/693 |
| 4,539,997 | 9/1985 | Wesseling et al. | 128/667 |
| 4,846,189 | 7/1989 | Sun | 128/667 X |
| 5,140,990 | 8/1992 | Jones et al. | 128/672 X |
| 5,152,297 | 10/1992 | Meister et al. | 128/672 |
| 5,282,467 | 2/1994 | Piantodosi et al. | 128/666 X |

*Primary Examiner*—Angela D. Sykes
*Attorney, Agent, or Firm*—Antonelli, Terry, Stout & Kraus

[57] ABSTRACT

Disclosed is a process and measurement device for noninvasive determination of venous and arterial blood pressure in the arteries of the human body, particularly in the finger and toes. An occlusion band and peripherally thereto a sensor for the detection of changes in the blood volume during the pressure-buildup procedure is attached in these measurement areas. The present invention is distinguished by the pressure-buildup procedure being characteriziend by a slow, preferably linear increase in air pressure in the occlusion band and the blood pressure values being determined from the change in the blood volume signal and the respective current occlusion pressure. It is possible for the first time to determine the venous pressure, the arterial diastolic pressure and the arterial systolic pressure bloodlessly during a single measurement test.

7 Claims, 5 Drawing Sheets

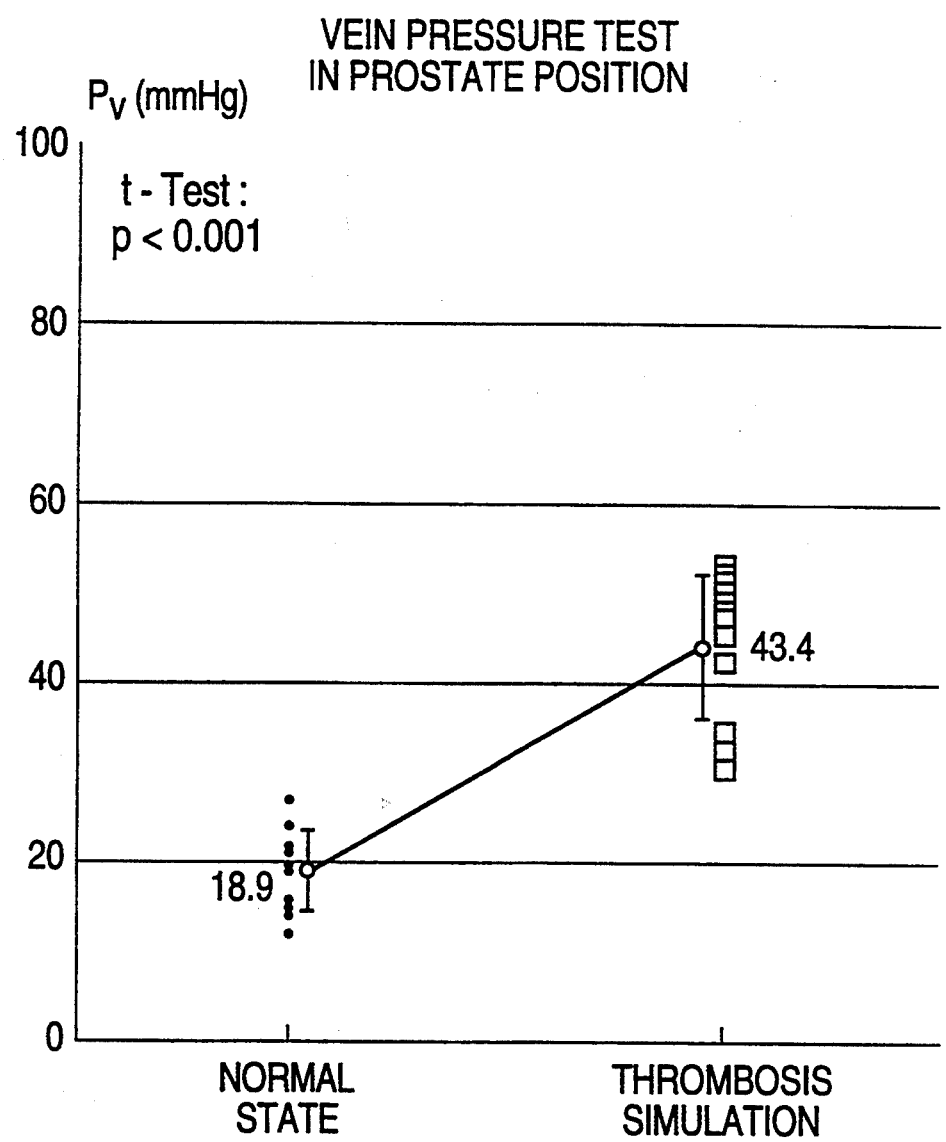

MEASUREMENT DEVICE FOR NON-INVASIVE DETERMINATION OF BLOOD PRESSURE IN THE VEINS AND ARTERIES

BACKGROUND OF THE INVENTION

The present invention relates to a device for non-invasive determination of blood pressure in the veins and arteries of fingers and toes.

Vascular diseases belong to the most common diseases in humans. Among these are, in particular, arteriosclerosis (calcium or fatty deposits in the arteries), dilation of veins (varicose veins) or vein blockage (thrombosis). There has been a need for a simple, bloodless method for determining the blood pressure especially in fingers and toes, because hemodynamic disturbances caused by the afore-mentioned diseases can already be detected in the early stages.

There are numerous state-of-the-art methods for measuring the peak (systolic $P_s$), bottom (diastolic $P_d$) or the average blood pressure of the arterial system, respectively during its temporal course. They all have in common that first a pressure-buildup band applied to the section of the limb (e.g., upper arm or finger) is quickly inflated in such a manner that its pressure $P_o$ exceeds $P_s$ within a few seconds. At this moment the outside pressure on the vessels beneath is greater than the pressure within them: they are closed. A slow reduction of $P_o$ follows. Lowering $P_o$ under $P_s$ permits a restricted flow of blood which causes the pulsating effect (e.g. Korotkoff tones in Riva-Rocci methods, pressure oscillation in the band in oscillometric methods or the return of pulsation in the reflection, respectively transmission signal in the photoplethysmographic method) known in the state of the art.

The primary drawback of these processes is that it is impossible to determine the blood pressure $P_v$ in the veins in this manner, which is of decisive significance for diagnosis.

In healthy humans in a prostrate position, the vein system may be termed. "low pressure system", i.e. the vein pressure $P_v$ only amounts to a few mmHg. When the venous blood flow between the measurement area and the heart is obstructed, e.g. in the case of acute thrombosis in the veins of the legs, the pressure $P_v$, on the other hand, is raised. In an upright position, the hydrostatic pressure components are added to these horizontal vein pressure values in the gravitational field of the earth so that the vein pressure in the lower parts of the body can increase substantially due to the redistribution of the blood volumes.

The object of the present invention is to provide a measurement device for non-invasive determination of blood pressure in the peripheral veins and arteries. An invented solution to this object with its improvements is set forth in the claims hereto. It is successful on the basis of a surprisingly simple fundamental idea: the reversal of the hitherto customary pressure process. Instead of the state-of-the-art procedure, rapid pressure buildup in the measurement band to $P_o > P_s$ and measured value search in the following measurement phase with slow pressure reduction, according to the present invention the pressure in the band is first built up slowly from 0 mmHg. The blood pressure values $P_v$, $P_d$ and $P_s$ are already determined in this preferably linear pressure build-up phase.

The present invention is made more apparent in the following using preferred embodiments with reference to the accompanying drawings to which moreover is to be referred for all invented details not made apparent in the text, without the intention of limiting the scope and spirit of the overall inventive idea.

BRIEF DESCRIPTION OF THE DRAWINGS

FIG. 5 illustrates results of the statistical evaluation of a measurement series of the pressure in the veins.

DESCRIPTION OF THE PREFERRED EMBODIMENT(S)

Figure 1:
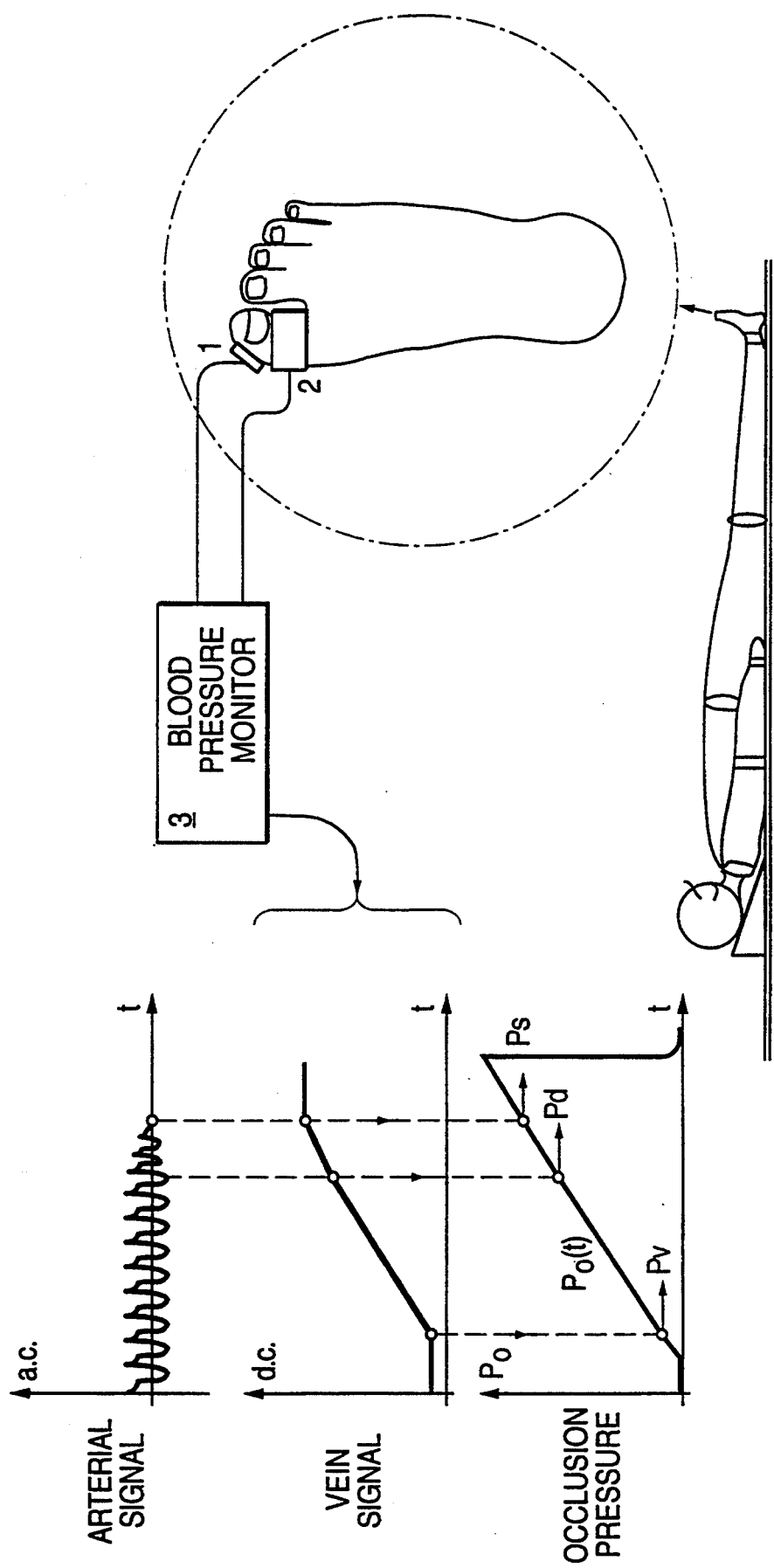
FIG. 1 illustrates the setup of the blood pressure measurement.

FIG. 1 shows a diagram of possible positioning of the patient and the attachment of sensors during the conduction of the blood pressure measurement including the typical measurement signals.

In this case, an air band (2) is applied to the big toe and peripheral to the air band a photoplethysmographic reflection sensor (1), in short PPG sensor, is applied. Both the air band and the PPG sensor are connected to the blood pressure monitor (3). At the output of the monitor, the three measured values can be recorded as a function of time: the occlusion pressure $P_o$ in the finger band, the vein signal (not pulsating d.c.—part of the reflection signal) and selectively also the artery signal (pulsing a.c.—part of the reflection signal). Blood pressure measurement is preferably conducted as follows: after the patient has been prepared and the band and the PPG sensor have been applied, measurement proceeds. Now the air pressure $P_o$ in the band is raised automatically, slowly and preferably linearly with a pressure gradient of approximately 4 mmHg/s. When $P_o = P_v$ the vein signal begins to rise because at this point the blood in the veins flowing from the toe through the band is obstructed. The pressure in the vein can thus be determined. The arterial inflow into the measured area peripheral to the band, however, is not yet impeded so that the vein signal initially continues to rise when the $P_o$ value increases slowly and the artery signal also registers the pulsating inflow of blood. The inflow of blood is not impeded by the band barrier until the occlusion pressure reaches the $P_d$ value of the pulsating arterial pressure. The result is a leveling off of the rise of the vein signal and the step-by-step reduction of the pulse amplitude of the artery signal. When finally $P_o > P_s$, the blood flow into the measured area is fully stopped. Both the arterial a.c. signal and the venous d.c. signal are now constant. All three blood pressure values $P_v$, $P_d$ and $P_s$ are unequivocally determined by the correlation of the d.c. signal with $P_o(t)$, and the band can now be deflated. Therefore, contrary to state-of-the art processes, also determining the arterial, a.c. signal in the invented device, is not vital.

Figure 2:
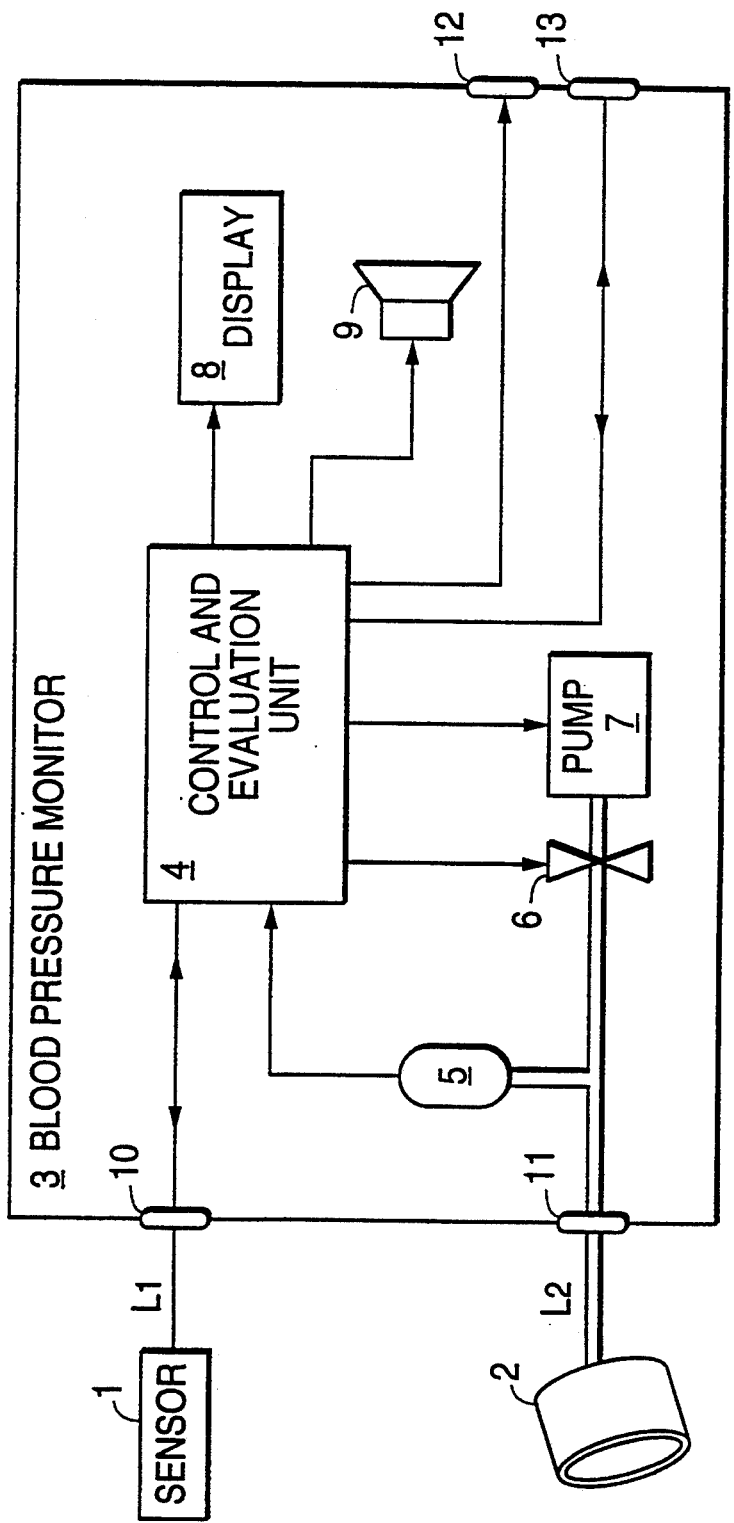
FIG. 2 illustrates a preferred embodiment of the present invention.

FIG. 2 shows a diagram of a preferred embodiment of the invented measurement arrangement. Sensor (1) is connected via the electric lead (L1) and plug (10) to the blood pressure monitor (3). And the band (2) is also connected to the blood pressure monitor (3) via the pneumatic plug (11) and the pneumatic lead (L2). The control and evaluation unit (4), which preferably is equipped with a microprocessor and analogue interfaces, first conducts first measurement procedures for calibrating the sensor signals (e.g. according to the teachings of P 42 12 498 A1) and to zero balance of the air pressure in the band with the aid of the pressure convertor (5) and the valve (6). During the actual measurement, the air pressure in the pneumatic system is raised in a controlled manner with the aid of the pump (7). The related measured signals (d.c. and Po, respectively d.c., a.c. and Po) are detected in this way. They can be shown on-line on a LC display (8) or recorded via an analogue (12) and digital (13) data output, respectively stored. During measurement, the examiner is supported by menu guidance on the display (8) or by acoustical signals of a built-in loudspeaker (9). When the sought blood pressure values are determined, the band is deflated, usually spontaneously (other deflation functions are also possible), and the measurement is completed. The described measurement procedure can be automatically repeated in short intervals as required so that the device can be utilized as a permanent blood pressure monitor in intensive-care medicine. Instead of the easy-to-handle and much proven-in-practice photoplethysmographic sensors, other types of sensors (e.g. according to the teachings of P 40 32 152 A1 or P 42 12 507 A1) may also be selectively utilized for detecting the vein signal.

Figure 3:
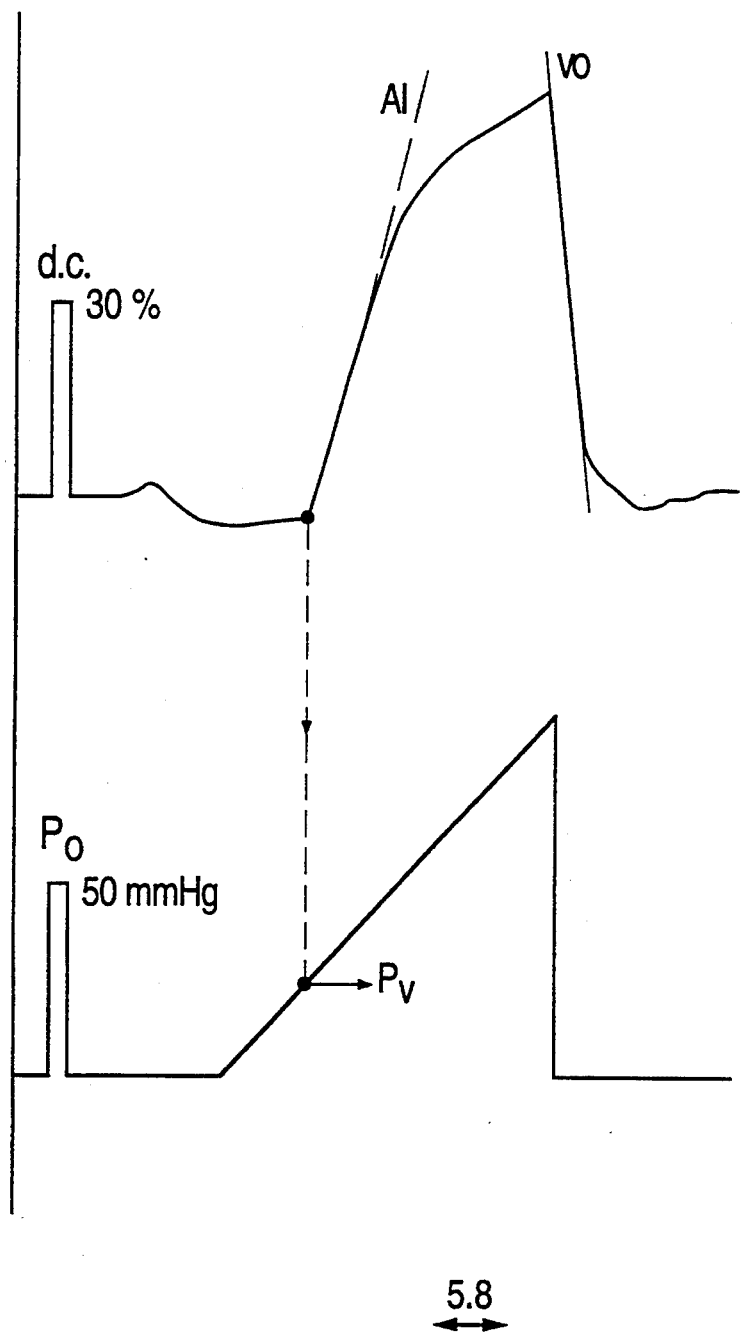
FIG. 3 and 4 illustrates various measurement records.

FIG. 3 shows typical recordings of vein signals of a PPG sensor and of the occlusion pressure as part of a vein pressure test measured at the left index finger of a reclining, sitting test person. The hand was in a horizontal position so that the index finger lies approximately at heart level. Allocating the d.c. signal rise to the band air pressure yields in this case a vein pressure of 22 mmHg. The maximum built-up pressure here is 90 mmHg. Further evaluation parameters that are of great interest for diagnosising thrombosis can also be determined from the d.c. curve: arterial inflow following the start of the pressure buildup AI=9%/s and vein flow-off following the end of the pressure buildup VO=20/%s.

Figure 4:
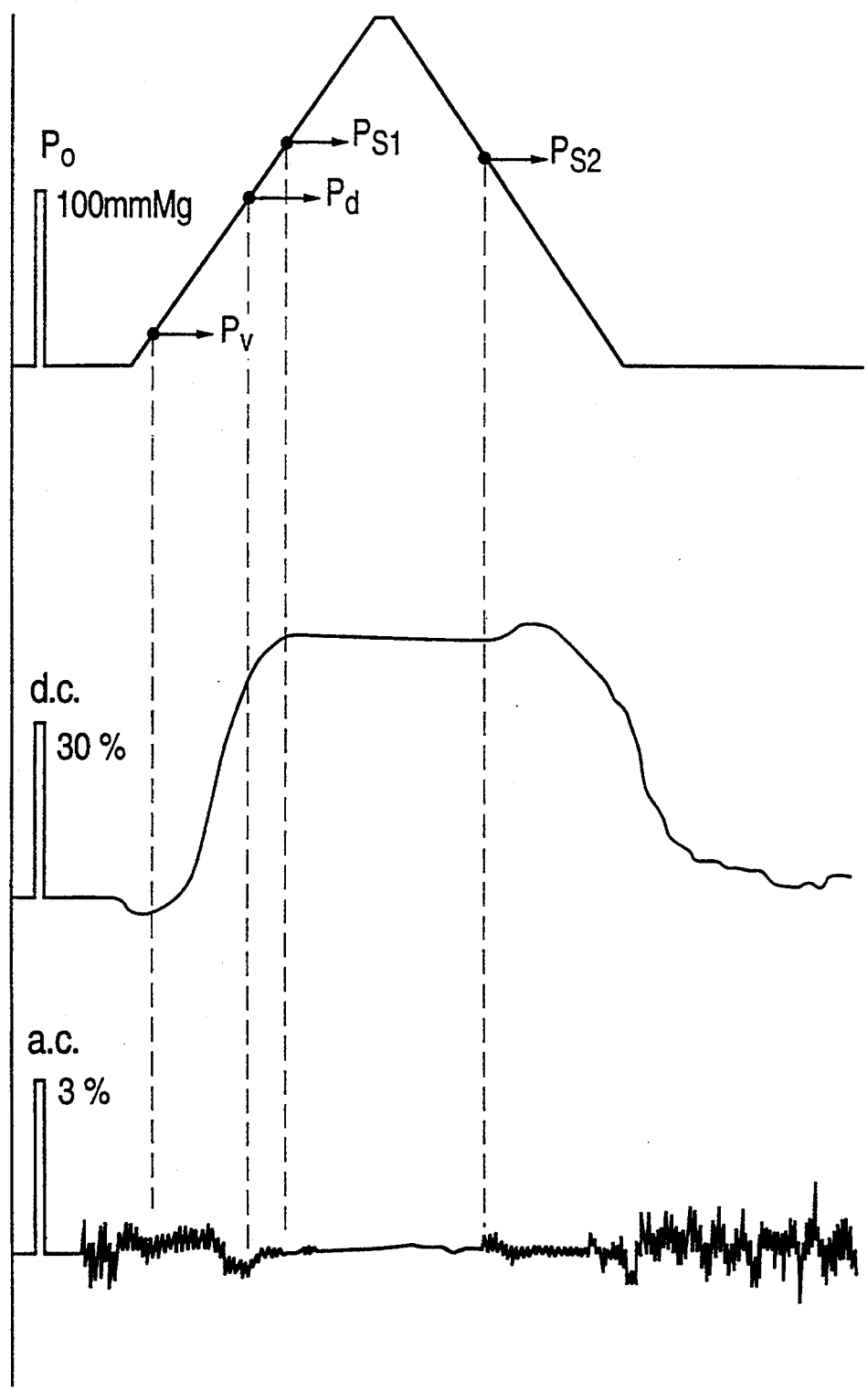

FIG. 4 shows an example of a measurement of all blood pressure values in the big toe of a reclining person. In this case, an occlusion programm was selected which provides slow, also linear band deflation instead of the obligatory abrupt deflation. In this mode of proceeding, the systolic blood pressure can be determined both from the ascent ($Ps_1$) as from the descent of Po(t) ($Ps_2$ value in FIG. 4).

Finally FIG. 5 shows the results of statistical evaluation of a measured series in which the peripheral pressure in the veins is determined in the big toe of 10 test persons in a prostrate position in a normal state and during a simulated thrombosis (intentionally brought about by means of an artificially builtup blockage in the thigh). In the case of all ten test persons, a raised vein pressure was measured during the thrombosis simulation. The average pressure rose significantly from originally 18.9 mmHg to 43.4 mmHg.

The present invention can, therefore, be utilized unrivaled in particular for early detection of thrombosis and in the case of all diagnosis in which vein pressure behavior influences the actual circulatory situation (e.g. in the study of the redistribution of the blood volume during space missions). The provided new measurement methods are at least equal to the state-of-the-art methods, however, also in the determination of arterial blood pressure values Pd and Ps.

What is claimed is:

1. A measurement device comprising a pressure-build-up band for attachment to an extremity for non-invasive determination of venous blood pressure values in said extremity; a pump for building up pressure in the pressure-build-up band; and a sensor for attachment to a finger or a toe peripherally to said pressure-build-up band, wherein said pump raises air pressure in said pressure-build-up band slowly starting at 0 mmHg and linearly with a pressure gradient of approximately 4 mmHg/s during a measurement phase and said device correlates a determination of said blood pressure values to detection of air pressure in said pressure-build-up band and a change in a vein signal detected using said sensor.

2. A device according to claim 1, wherein a reduction in pressure following an end of a pressure buildup is conducted abruptly.

3. A device according to one of claims 1 to 2, wherein an
   inflating and deflating of said pressure-build-up band during determination Of said blood pressure values is automatically conducted according to predetermined routines.

4. A device according to one of claims 1 to 2, wherein change in said air pressure in said pressure-build-up band is carried out by said device further comprising:
   an electronically controlled pump, a valve and control and evaluation electronics for controlling said pump and said valve.

5. A device according to claim 4, wherein
   said control and evaluation electronics automatically calibrates signals of said sensor and correlates said signals to said air pressure in said pressure-build-up band and automatically detects a pressure in veins Pv and arterial blood pressure values Pd and Ps.

6. A device according to claim 4 wherein said control and evaluation electronics is equipped with a microprocessor and can simultaneously control several sensors and/or bands in such a manner that a segmental or contralateral detection of said blood pressure values is possible.

7. A device according to one of claims 1 to 2, wherein
   said sensor operates according to a photoplethyemographic measurement principle in at least one of a reflection and transmission mode and is provided with at least one light emitter and one light detector.

* * * * *